United States Patent [19]

Pelloso et al.

[11] Patent Number: 5,434,278
[45] Date of Patent: Jul. 18, 1995

[54] SYNTHESIS OF ACETOGLYCERIDE FATS

[75] Inventors: Turiddu A. Pelloso, Carmel; Allan D. Roden, Noblesville; Gilbert L. Boldt, Indianapolis, all of Ind.

[73] Assignee: Nabisco, Inc., Parsippany, N.J.

[21] Appl. No.: 12,712

[22] Filed: Feb. 3, 1993

Related U.S. Application Data

[63] Continuation-in-part of Ser. No. 804,140, Dec. 6, 1991, Pat. No. 5,258,197, which is a continuation-in-part of Ser. No. 624,056, Dec. 7, 1990, abandoned, which is a continuation-in-part of Ser. No. 410,161, Sep. 20, 1989, abandoned.

[51] Int. Cl.⁶ .................... C11C 3/10; C07C 51/00; C07C 55/22
[52] U.S. Cl. ..................................... 554/165; 554/169
[58] Field of Search ................................. 554/165, 169

[56] References Cited

U.S. PATENT DOCUMENTS

| | | |
|---|---|---|
| 2,615,159 | 10/1952 | Jackson . |
| 2,615,160 | 10/1952 | Baur . |
| 2,808,421 | 10/1957 | Brokaw ............................... 554/169 |
| 3,192,057 | 6/1965 | Hines . |
| 3,388,085 | 6/1968 | Levkoff et al. . |

FOREIGN PATENT DOCUMENTS

| | | |
|---|---|---|
| 53-000208 | 1/1978 | Japan . |
| 822730 | 10/1959 | United Kingdom . |

OTHER PUBLICATIONS

Bailey's Industrial Oil and Fat Products, 4th ed., J. Wiley, New York, 1979, vol. 1, pp. 16–17.
Baur, F. J., J. Amer. Oil Chem. Soc. 31: 147–151 and 196–199 (1954).
Bonanome, A. And Grundy, S. M., New Eng. Jour. Med. 318: 1244–1248 (1988).
Cummings, J. H., Cut 22:763–779 (1981).
Feuge, R. O., Food Technology 9: 314–318 (1955).
Feuge, R. O., et al., J. Amer. Oil Chem. Soc. 29: 11–14 (1952).
Feuge, R. O. and Bailey, A. E., Oil and Soap 23: 259–264 (1946).

*Primary Examiner*—José G. Dees
*Assistant Examiner*—Dwayne C. Jones

[57] ABSTRACT

Acetoglycerides are prepared in a solventless, single phase interesterification between triacetin and triglycerides bearing long $C_{16}$ to $C_{22}$ fatty acid residues by adding triglycerides bearing saturated $C_3$ to $C_{10}$ acid residues to the reaction mixture. The long acid residues may be hydrogenated before or after interesterification. In one embodiment, the $C_3$ to $C_{10}$ triglycerides are tripropionin, tributyrin, or mixtures of these; in another, these are triglycerides bearing $C_8$ to $C_{10}$ acid residues; and in a third, these are a mixture of tripropionin and/or tributyrin and $C_8$ to $C_{10}$ triglycerides. In preferred embodiments, the molar ratio of $C_{16}$ to $C_{22}$ triglycerides to triacetin and $C_3$ to $C_{10}$ triglycerides varies between 1:1 and 1:15, more narrowly between 1:3 and 1:12, and high temperatures are employed. The process diminishes catalyst use, obviates the need for high shear mixing, shortens reaction times, and simplifies purification steps.

28 Claims, No Drawings

SYNTHESIS OF ACETOGLYCERIDE FATS

RELATED U.S. APPLICATION DATA

This is a continuation-in-part of U.S. application Ser. No. 804,140, filed Dec. 6, 1991, now U.S. Pat. No. 5,258,197, issued Nov. 2, 1993, hereby incorporated in its entirety by reference, which was a continuation-in-part of U.S. application Ser. No. 07/624,056, filed Dec. 7, 1990, now abandoned, which was a continuation-in-part of U.S. application Ser. No. 07/410,161, filed on Sep. 20, 1989, now abandoned.

TECHNICAL FIELD

This invention relates to an improved process for preparing triglycerides bearing short, e.g., acetyl, and long, saturated ($C_{16}$ to $C_{22}$) residues.

Interesterifications involving long chain triglycerides such as tristearin and tripalmitin have been recognized for decades as posing solubility problems (U.S. Pat. No. 2,442,531 to Eckey), so that solvents or some other means are needed to cope with the phases formed to put the reactants in contact with each other. Because of the nonmiscible nature of triacetin, the problem is compounded in interesterification reactions using it as a reactant with long chain triglycerides because the nature of the starting materials are so disparate.

The short chain fatty acids, acetic, propionic, and butyric acid, also called, as a group, volatile fatty acids, occur in the large intestine of all mammalian species so far studied (Cummings, J. H., *Gut* 22: 763–779 (1981), but, except for a small percentage of butyric acid in milk fat, they rarely occur in nature esterified to glycerol. Instead, they are free by-products of fermentation in the gut. Physically, short chain fatty acids "are not at all 'fatlike' in character; in fact, they are hydrophilic substances with complete miscibility with water" (*Bailey's Industrial Oil and Fat Products*, 4th. ed., J. Wiley, New York, 1979, volume 1, pages 16 to 17).

Therefore, interesterification reactions between long chain triglycerides and triglycerides bearing short chain residues generally involve the use of solvents and/or high levels of catalyst, and long reaction times. Solvents and high levels of catalysts employed in the reactions are difficult to separate from the final product, can contribute undesirable flavors and may even have toxic properties, limiting the usefulness of such syntheses for edible fats. Moreover, use of solvents and high levels of catalyst in addition to starting materials represents expense in storage, handling and recovery, and necessitates complicated and costly purification steps subsequent to formation of reaction products. Long reaction times lead to oxidation and contribute to side reactions.

It would be desirable to have an efficient solventfree preparation of triglycerides bearing short and saturated and/or unsaturated, long chain residues.

BACKGROUND ART

During the 1950's, fat products were produced by substituting, in effect, acetic acid for a portion of the fatty acids occurring in ordinary fats and oils so as to obtain predominantly either monoaceto or diaceto triglycerides or combinations of these (Feuge, R. O., *Food Technology* 9: 314–318 (1955)), or mixtures of these triglycerides with mono- or diaceto diglycerides. The fats were called acetoglycerides, and most of the publications (from two groups of investigators working independently) described acetostearins (ibid.).

Acetostearins are waxy fats having sharp melting points, which has limited their application in food products requiring more plastic or liquid fats. One study described the fats as "highly flexible" and elastic; at a temperature of 22° C., they could be stretched more than 800% (Feuge, R. O., et al., *J. Amer. Oil Chem. Soc.* 29: 11–14 (1952)). When chewed in the mouth, diacetostearin has been described as "somewhat like a gum" (U.S. Pat. No. 2,615,160 to Baur, column 7, line 55). In contrast to fats bearing medium and/or long substituents, acetostearins also exhibit unusual polymorphism (Baur, F. J., *J. Amer. Oil Chem. Soc.* 31: 147–151 and 196–199 (1954) and the Feuge *Food Technology* paper cited above).

Because of the waxy, rubbery functional properties of the fats, they were suggested for use in candy, as well as in icings and frostings, in spray oils for crackers, in edible "beeswax" for synthetic honey, in chewing gum, and in protective coatings for products such as fruits, cheese, preserves, and meats (U.S. Pat. No. 2,615,160, column 7, lines 59 to 64). But in the intervening decades, waxy acetoglycerides have been primarily used as protective coatings, thin films, moisture barriers and plasticizers. The protective coatings are sometimes called "hot melts" and may contain antibiotics (U.S. Pat. No. 3,192,057 to Hines and Shirk) or polymeric materials (U.S. Pat. No. 3,388,085 to Levkoff and Phillips) to prolong the life of the coating.

Recent research in this laboratory has shown that acetoglyceride-type fats bearing long ($C_{16}$ to $C_{24}$), saturated pendant groups and short groups such as acetyl as well as propionyl and butyryl are low in calories, and their functional properties can De modified for a variety of edible uses (U.S. application Ser. No. 07/804,140, now U.S. Pat. No. 5,258,197 issued Nov. 2, 1993, cited above). Therefore, it would be desirable to have new and improved processes for making these types of fats.

The Feuge, et al., group of investigators at the Southern Regional Research Laboratory prepared acetostearins by acetylating stearins with acetic anhydride (Feuge, R.O., et al., *J. Amer. Oil Chem. Soc.* 29: 11–14 (1952)). Other acetoglycerides were prepared by converting starting material fats to mono- and diglycerides, generally by mixing them with glycerol and sodium hydroxide for 0.3 to 3 hours at 200° to 250° C. (*Food Technology*, cited above, at page 314, column 2, paragraph 1). The resulting technical grade mixture is then acetylated directly or purified and acetylated. To obtain a homogeneous reaction product for later acetylation, in some cases the glycerol reaction was conducted in the presence of phenol or cresol (Feuge, R. O., and Bailey, A. E., *Oil and Soap* 23: 259–264 (1946)). Difficulty was experienced in freeing the product of solvent without decomposition of the glycerides (ibid.).

Although acetylation of stearins with acetyl chlorides in chloroform in the presence of pyridine was employed to make acetostearin isomers (U.S. Pat. No. 2,615,159 to Jackson, column 2, lines 1 to 4), the Baur group generally employed an interesterification reaction to obtain acetostearin mixtures (U.S. Pat. No. 2,615,160). Triacetin was reacted with a conventional fat in the presence of a low temperature rearrangement catalyst such as sodium alkoxide suspended in xylene or other low-boiling hydrocarbon which is miscible with the fats (id., column 2, lines 22 to 32 and column 3, lines 8 to 10). Thus, the system used had two phases.

Reaction temperatures were fairly low because higher ones impaired catalyst activity (id., column 3, lines 26 to 28). The level of catalyst used at these temperatures had to be relatively high, and the amount had to be increased where less well processed feedstocks that poisoned the catalyst were employed. High shear during mixing of the reaction was also necessary to emulsify the two nonmiscible phases. The ratios of triacetin to fat employed were low (35:100 to 50:100 in the examples, columns 5 to 6), which limited the variety of acetoglycerides obtained with the method. Unreacted triacetin was removed by water washing so that a large percentage of triacetin was washed out with the waste water. Products were purified by distillation.

It would be desirable to have a process for preparing acetoglyceride fats for edible use that was free of potentially toxic or noxious solvents, and that eliminated the need for costly purification steps. It would also be desirable to have an efficient, economical process that minimized catalyst use and losses of starting materials.

DISCLOSURE OF THE INVENTION

It is an object of the invention to provide a solventless process for the preparation of acetoglyceride fats in a single phase reaction.

It is a further object of the invention to provide a process that requires lower levels of catalyst and shorter reaction times.

It is another object of the invention to provide neat catalyst addition and higher reaction temperatures that lower production costs.

These and other objects are accomplished by the present invention which provides a solventless, single phase process for synthesizing triglycerides bearing acetyl and long $C_{16}$ to $C_{22}$ fatty acid residues which comprises interesterifying triglycerides bearing long $C_{16}$ to $C_{22}$ fatty acid residues with a mixture of triacetin and triglycerides bearing saturated $C_3$ to $C_{10}$ acid residues. In one embodiment, long chain triglycerides are interesterified with triacetin and tripropionin or tributyrin or a mixture of tripropionin and tributyrin. In another embodiment, long chain triglycerides are interesterified with triacetin and triglycerides bearing $C_8$ to $C_{10}$ acid residues. In a third embodiment, long chain triglycerides are interesterified with triacetin and a mixture of tripropionin and/or tributyrin and triglycerides bearing saturated $C_8$ to $C_{10}$ acid residues. If the long chain triglycerides are not fully saturated, the acetoglyceride products may be hydrogenated after interesterification.

Especially preferred are interesterication reactions wherein the reactant molar ratio of triglycerides bearing long $C_{16}$ to $C_{22}$ fatty acid residues to triacetin and triglycerides bearing $C_3$ to $C_{10}$ acid residues varies between 1:1 and 1:15, more narrowly between 1:3 and 1:12. The molar ratio of triacetin to triglycerides bearing $C_3$ to $C_{10}$ acid residues such as tripropionin in these reactions can be as high as 40:1, but typically the upper limit is 24:1. In many embodiments, this molar ratio varies between 1:11 to 11:1.

In some embodiments, at least about 70%, preferably at least about 85%, and in some embodiments at least about 92% of the fatty acid residues in the triglycerides bearing long $C_{16}$ to $C_{22}$ fatty acid residues are $C_{18}$ acid residues. These may be hydrogenated before or after the reaction.

BEST MODE FOR CARRYING OUT THE INVENTION

This invention is based upon the surprising finding that adding triglycerides bearing saturated $C_3$ to $C_{10}$ acid residues such as tripropionin to an interesterification reaction between triacetin and triglycerides bearing long $C_{16}$ to $C_{22}$ fatty acid residues yields a single phase so that the reaction can be conducted rapidly in the absence of solvents or high shear mixing.

In the practice of this invention, triglycerides bearing long $C_{16}$ to $C_{22}$ fatty acid residues are interesterified, in the absence of solvents, with triacetin and triglycerides bearing saturated $C_3$ to $C_{10}$ acid residues for such time under such conditions that triglycerides bearing acetyl, $C_3$ to $C_{10}$, and long residues form.

By "interesterification" is meant a reaction of triacylglycerol structures whereby individual positions of esterified fatty acids are interchanged on the glyceryl moiety. These reactions are generally initiated by adding a catalyst, and heating up to about 80° C. with agitation for such time under such conditions that the reaction occurs.

By the term "solvent" is meant a material that is liquid at the synthesis reaction temperature pressure and will dissolve, suspend or hold triacetin and fully hydrogenated fats in the reaction to expedite contact for the desired interesterification without taking part or being consumed in the reaction, such as for example, xylene.

Interesterification catalysts include, but are not limited to, alkali metals such as sodium or potassium or a mixture or alloy of these, alkali metal hydrides, alkali metal alkoxides such as sodium methoxide, potassium methoxide, lithium methoxide, sodium ethoxide, potassium ethoxide, lithium ethoxide, sodium propoxide, potassium propoxide, lithium propoxide, sodium butoxide, potassium butoxide, lithium butoxide, and the like. Other interesterification catalysts used by the skilled artesan may also be employed.

Triglycerides bearing long $C_{16}$ to $C_{22}$ fatty acid residues are generally obtained from natural oils such as soybean, safflower, sunflower, sesame, peanut, corn, olive, rice bran, mustard seed, cottonseed, poppyseed, rapeseed, marine, meadowfoam and the like oils; fats such as palm oil, tallow, lard, and shea butter; or plant waxes such as jojoba. Fat mixtures and/or fractions, crystallized fats, interesterified fats and mixtures of these may also be employed, as can synthetic fats such as tristearin and palmitostearin. The long triglycerides may be hydrogenated before or after the interesterification reaction.

It is an advantage of the invention that hydrogenated fats can be employed as reactants, including fully hydrogenated fats, i.e., fats hydrogenated to an Iodine Value of 5 or less, and, in some cases, less than 2. Preferred reactants for some embodiments are fully hydrogenated fats having at least about 70 weight %, preferably at least about 75 weight % stearic acid residues such as, for example, hydrogenated peanut, olive, soybean, seasame or corn oil, or mixtures of these are especially desirable. Some embodiments employ fats having at least about 90 to 92 weight % stearic acid residues, such as hydrogenated sunflower oil, safflower oil or canola, or mixtures thereof. Others can employ a mixture of hydrogenated oils having pendant groups exhibiting greater chain length variety, such as, for example, a mixture of hydrogenated canola or soybean oil and rapeseed oil, hydrogenated canola or soybean oil and cottonseed oil, and the like. Using fully hydrogenated feedstocks is advantageous because they yield products low in trans unsaturation.

Because there is evidence that palmitic acid (like lauric and myristic acids) may increase plasma cholesterol concentrations (Bonanome, A., and Grundy, S. M., *New Eng. Jour. Med.* 318:1244–1248 (1988)), preferred hydrogenated feedstocks in these embodiments are low in palmitic acid content. However, it is an advantage of the invention that those that are not yield fat products having decreased palmitic acid contents since the acetyl and saturated $C_3$ to $C_{10}$ residues replace a significant portion of palmitic acid in the feedstock.

Long, saturated $C_{16}$ to $C_{22}$ fatty acid residues include, but are not limited to, palmitic (hexadecanoic), stearic (octadecanoic), arachidic (eicosanoic), behenic (docosanoic), and the like acid residues. These residues may also be derived by hydrogenating fats or oils containing unsaturated acids such as, for example, palmitoleic (9-hexadecenoic), oleic (cis-9-octadecenoic), elaidic (trans-9-octadecenoic), vaccenic (trans-11-octadecenoic), linoleic (cis, cis-9,12-octadecadienoic), linolenic (9,12,15-octadecatrienoic and 6,9,12-octadecatrienoic), eleostearic (9,11,13-octadecatrienoic), arachidonic (5,8,11,14-eicosatetraenoic), and the like.

Saturated $C_3$ to $C_{10}$ triglycerides include any triglycerides bearing propionic, butyric, caproic, caprylic, pelargonic, and/or capric short or medium acid residues such as, for example, tripropionin, tributyrin, tricaproin, tricaprylin, tripelargonin and tricaprin, and any mixtures or combinations of these. In one embodiment, tripropionin, tributyrin or mixtures of these are employed. Another embodiment employs triglycerides bearing mixtures of $C_8$ to $C_{10}$ acid residues. A third embodiment employs a mixture of tripropionin and/or tributyrin with mixtures of triglycerides bearing $C_8$ to $C_{10}$ acid residues. As used herein, chemical names include isomeric variations; for example, "butyric acid" includes normal-butyric acid (butanoic) and iso-butyric (2-methylpropanoic) acid, and so forth.

Acetoglyceride fats are prepared by mixing triglycerides bearing long residues with those bearing saturated $C_3$ to $C_{10}$ triglycerides and triacetin, heating and agitating in the presence of catalyst. High temperatures are preferred, i.e., temperatures varying between 100° C. and 150° C., more preferably, between about 120° C. and 135° C. It is an advantage of the invention that the high temperature reaction allows use of less catalyst, which reduces the cost of production. In addition, the use of less catalyst and less active catalyst means that refining losses are lower and, with fewer catalyst poisoning problems, less well processed feedstocks can be used. High shear mixing is not required.

It is a further advantage of this invention that the reactants can be mixed or slurried together in any order or combination. This further reduces the need for high levels of catalyst, reduces the need for high shear mixing, and speeds reaction time, which can be as short as five minutes. In the absence of solvent, catalyst can be added neat, which removes the need for explosion-proof rooms and reactors. Unreacted triacetin and short and medium triglycerides can be returned to the reaction vessel neat, facilitating reactant recycling in some processes. It is another advantage of the solventless process that solvent contamination issues, particularly purification steps to provide fats for edible compositions, are eliminated. The process yields products free of potentially toxic or noxious solvents.

It is a further advantage of the invention that high short to long reactant molar ratios can be employed, providing a great diversity of acetoglyceride products made using the process. In some embodiments, for example, the molar ratio of triglycerides bearing long $C_{16}$ to $C_{22}$ fatty acid residues to triacetin and tripropionin, triacetin to tributyrin, or triacetin to tripropionin and tributyrin varies between 0.1:1 and 1:1. However, in other embodiments, the same molar ratio varies between 1:1 and 1:15, more narrowly between 1:3 and 1:12.

It is another advantage of the solventless process of the invention that water washing is not needed for product purification. Water washing removes triacetin starting material, and this reduces recycling of unreacted product and increases operating costs. Water washing also increases refining problems. In addition, the process of this invention does not require vacuum distillation as a purification step. Edible fat products can be prepared by interesterification followed by steam deodorizationo By using high temperatures and eliminating solvents, catalyst use is diminished, reaction times and yields are improved, and purification steps are simplified so that the process of the invention is both efficient and economical.

EXAMPLES

The following examples are presented to further illustrate and explain the present invention and should not be taken as limiting in any regard. Unless otherwise indicated, all parts and percentages are by weight, and are based on the weight at the particular stage of the processing being described. Solid fat indices (herein abbreviated S.F.I.) are determined using dilatometry according to A.O.C.S. Method Cd 10–57 (1989), reporting solids at 50° F. (10° C.), 70° F. (21.1° C.), 80° F. (26.7° C.), 92° F. (33.3° C.), a 100° F. (37.8° C.). Solid fat contents (herein abbreviated S.F.C.) are determined using nuclear magnetic resonance (NMR) according to A.O.C.S. Method Cd 16–81, and are reported for the same temperatures as S.F.I. values unless otherwise indicated. Mettler dropping points (M.D.P.) are determined using a Mettler Thermosystem FP 800 following A.O.C.S. Method Cc 18–80 (1989).

EXAMPLE 1

This example illustrates the difficulty of preparing acetoglycerides using standard interesterification procedures.

An attempt is made to interesterify 2.5 moles triacetin with 1 mole hydrogenated canola (899 g refined, low erucic rapeseed oil containing ≦4% palmitic acid, hydrogenated at 180° C. and 60 lbs hydrogen until the Iodine Value (IV) is ≦3). After agitation of the reactants, two individual phases could be seen. Catalyst is added (0.2 to 0.3% sodium methoxide) and the mixture is heated to ~110° C. under a vacuum for about half an hour. Two individual phases are observed. Phosphoric acid (~0.2 to ~0.5%, at least twice the amount of sodium methoxide) is added to stop the reaction and neutralize the mixture, followed by the addition of 0.5% activated bleaching clay (Tonsil Optimum FF), 0.5% diatomaceous earth, and 1000 ppm citric acid (dissolved in water) to decolorize and remove soaps. The treatment is continued for ½ to 1 hour at 110° C. The M.D.P. before the attempted reaction is 66.5° C., and after reaction it is 64.2° C. to 64.4° C. No reaction between reactants occurs; only a side reaction of canola interesterification is seen.

The triacetin-hydrogenated canola interesterification reaction is repeated using 12 moles of triacetin and twice the amount of catalyst. Again, two phases are observed, and, instead of dropping, the M.D.P. increases from 29.8° C. to 35.7° C. No reaction between the triacetin and the canola is observed.

The triacetin-hydrogenated canola interesterification reaction is repeated using 8 moles triacetin, about four times the amount of catalyst (0.8%), a higher reaction temperature (130° C.), and a longer reaction time (1.5 hours). The M.D.P. again increases from 31.0° C. to 36.8° C., indicating that no reaction between the triacetin and the canola occurred, but the resulting mixture still separated into two phases. After steam deodorization, the S.F.C. of the product, apparently a mixture of unreacted and interesterified canola, is 89.7% at 50° F., 87.9% at 70° F., 85.4% at 80° F., 24.2% at 92° F., 0.3 at 100° F.

EXAMPLE 2

This example illustrates the preparation of acetoglycerides using the method of U.S. Pat. No. 2,615,160 to Baur set out in the patent's Example 1, column 5, lines 37 to 62, which involves the interesterification of triacetin with cottonseed oil followed by hydrogenation, denoted Sample A below, and Example 2, column 6, lines 6 to 22, which involves the interesterification of hydrogenated soybean oil with triacetin, denoted Sample B below. Every effort is made to reproduce the examples, and several attempts are made to ensure that the work is reproduced correctly.

Sample A.

The interesterification reaction is conducted in three batches because larger batches failed to react due to the requirement for much higher shear mixtures. One hundred parts refined, bleached, and dried cottonseed oil (2000 gms obtained from Humko) are mixed with 50 parts triacetin (1000 gms obtained from Aldrich). This is heated to 110° C. under vacuum to remove moisture picked up in transit by the materials. This is then cooled to 90° F. and 0.6 parts sodium methylate (30 gms supplied by Mallinkrodt) in xylene (150 gms) is added. Random rearrangement of acyl radicals is allowed to proceed with agitation of the mixture for one half hour, after which time glacial acetic acid (50 gms) is added. The material is then water washed.

This procedure is repeated again. A third batch is prepared using 1100 gms of cottonseed oil and 550 gms triacetin. The batches are combined and steam distilled under a pressure of 1 to 2 mm mercury (145° C., steam distillation temperature being defined as the vapor temperature taken at the discharge of the vessel) to remove low boiling constituents. The temperature of the distillation is then increased to 200° to 250° C. in order to remove the higher molecular weight diacetyl triglycerides. The distillate is collected separately and amounts to 27.44% of the original blend of material, which compares well with Baur's yield of 32%. The material is analyzed by super critical fluid chromatography and found to contain more than 90% diacetyl triglycerides.

The distillate which appears to be mono-oleyl diacetin triglycerides is next hydrogenated to an iodine value of 0.47. This is accomplished in a Parr bomb with 1880 gms distillate and 5.7 gms of (Nysosel TM 325) nickel catalyst. The reaction is carried out at 180° C. under hydrogen pressure of less than 50 psi.

On cooling to about 20° C., the product solidifies to a waxy, rubbery, translucent form having a complete melting point of 31.3° C., identical to Baur's (column 5, line 66), and a calculated saponification value of 370 mg of potassium hydroxide/gm, which compares well with Baur's experimental saponification value of 375 (column 5, line 67). The sample contains traces of triacetin.

Sample B.

Hydrogenation of refined, bleached and dried soybean oil is carried out to practical completion by charging a Parr bomb with 2200 gms refined, bleached soy oil (obtained from Humko) and adding 6.6 gms nickel catalyst (Nysosel TM 325) along with 6.6 gms of filter aid. The oil is heated to 175° C. under nitrogen pressure. The nitrogen is then evacuated, hydrogen gas is bubbled through the oil, and the pressure in the reactor increased to a maximum of 50 psi. After 3 hours, the batch is allowed to cool and the material removed from the reactor. The material is then post bleached by adding 500 ppm citric acid and bleaching clay (Tonsil Optimum FF). The clay is removed by filtration to produce a bleached, fully hydrogenated soy oil with an iodine value of less than 1.5 and a melting point of greater than 67° F. This process is repeated three additional times to produce enough material.

One hundred parts (2000 gms) of the dried hydrogenated soybean oil is melted and mixed with 35 parts (700 gms) of dry triacetin and the acyl groups of the mixture are molecularly rearranged under the catalytic influence of 6.75 parts (13.5 gms) of sodium methylate as in the production of sample A above. The catalyst is inactivated with the acetic acid, and the acidified mixture is alkali refined with 14° Be lye. This reaction, in the same ratios, is repeated a second time, the only change being the addition of extra catalyst to force the reaction to completion.

The residual unreacted triacetin is removed by steam distillation as in the sample A preparation above (i.e., steam distillation at 145° C. under a pressure of 1 to 2 mm of mercury). Diacetyl glycerides are then distilled off at a pot temperature of 230° C. under a pressure of 2–3 mm of mercury (for a period of 6 hours). Raising the pot temperature to 250° C. increases the yield to about 30% which compares well with Baur's reported yield of 31% (column 6, line 20).

Using differential scanning calorimetry, the soft, waxy, rubbery product exhibits an estimated complete melting point of about 35° C., comparing favorably with Baur's reported value of 32.8° C. (column 6, line 26) using different methodology. The sample contains traces of triacetin.

EXAMPLE 3

This example illustrates the preparation of acetoglycerides using the method of this invention, and a comparison of the method with Baur's process set out in Example 2.

Acetoglyceride fat mixtures are prepared using the interesterification procedure of Example 1, except that the interesterification mixture contains hydrogenated canola with both tripropionin (1.25 moles, 2.25 moles and 6 moles per mole hydrogenated canola) and triacetin (in the same proportions), the reaction temperature is 120° to 125° C., and 0.2 to 0.5% sodium methoxide is employed. Though reactions are run for about 5 to 30 minutes, most are complete in less than 10 minutes. The samples are steam deodorized after interesterification as set out in Example 1.

Using these preparative procedures, the following M.D.P. and S.F.I. data on the products are obtained:

| Hydrogenated Canola:Tripropionin:Triacetin Reactant Molar Ratio | | | |
|---|---|---|---|
| | 1:1.25:1.25 | 1:2.25:2.25 | 1:6:6 |
| M.D.P., °C. | 36.8 | 33.8 | 31.4 |
| S.F.I. 50° F. | 71.4 | 69.8 | 54.8 |
| 70° F. | 69.8 | 56.0 | 34.2 |
| 80° F. | 64.3 | 1.5 | 0.0 |
| 92° F. | 23.0 | 0.0 | 0.0 |
| 100° F. | 0.2 | 0.0 | 0.0 |

The interesterifications are repeated, except that the interesterification mixture contains different proportions of hydrogenated canola (abbreviated "H-Canola"), tripropionin and triacetin. The following data are obtained:

| H-Canola:Tripropionin:Triacetin Reactant Molar Ratio | | |
|---|---|---|
| | 1:1:11 (C) | 1:11:1 (D) |
| M.D.P., °C. | 35.0 | 17.6 |
| S.F.I. 50° F. | 64.4 | 55.0 |
| 70° F. | 62.4 | 32.3 |
| 80° F. | 58.7 | 7.4 |
| 92° F. | 28.5 | 0.0 |
| 100° F. | 0.4 | 0.0 |

Proton NMR shows that sample C contains 51 mole % acetyl, 13 mole % propionyl and 36 mole % long acid residues. Sample D contains 7 mole % acetyl, 57 mole % propionyl, and 36 mole % long acid residues.

The procedure is repeated using different hydrogenated feedstocks. Interesterification of 11 moles triacetin, 1 mole tripropionin, and 1 mole hydrogenated soybean oil followed by steam deodorization yields a fat product having a M.D.P. of 34.8° C. and an S.F.I. of 69.2% at 50° F., 68.2% at 70° F., 64.5% at 80° F., 4.0% at 92° F., and 0% at 100° F. Interesterification of 1 mole triacetin, 11 moles tripropionin, 0.9 mole hydrogenated canola, and 0.1 mole hydrogenated high erucic rapeseed oil followed by deodorization yields a product having a M.D.P. of 31° C. and an S.F.I. of 64.6% at 50° F., 53.1% at 70° F., 26.2% at 80° F., and 0% at 92° F. Interesterification of 11 moles triacetin, 1 mole tripropionin, 0.9 mole hydrogenated canola, and 0.1 mole hydrogenated high erucic rapeseed oil followed by deodorization yields a product having a M.D.P. of 35.4° C. and an S.F.I. of 70.2% at 50° F., 68.4% at 70° F., 63.8% at 80° F., 33.1% at 92° F., and 0.2% at 100° F. Interesterification followed by deodorization of 5 moles triacetin, 3 moles tripropionin, 0.9 mole hydrogenated canola, and 0.1 mole hydrogenated high erucic rapeseed yields a product with a M.D.P. of 33° C. and an S.F.I. of 68.7% at 50° F., 64.1% at 70° F., 52.3% at 80° F., 7.2% at 92° F., and 0% at 100° F.

All the interesterifications take place in a single phase reaction medium. All employ relatively low levels of catalyst, and the catalyst is added neat. All reactions employ relatively high temperatures. All employ relatively high reactant molar ratios of short to long triglycerides. None require high shear mixing. Unreacted short triglycerides can be recovered neat so that recycling is possible.

In contrast, the Baur procedures set out in Example 2 are two-phase reactions. They employ a solvent and relatively high amounts of catalyst. The reaction times are longer. The water washing increases loss of triacetin starting material, and thus cost of production. And only relatively low reactant molar ratios of short to long triglycerides can be employed in the reaction, which limits the functionality of the fats obtained in the synthesis.

EXAMPLE 4

This example illustrates the synthesis of another type of acetoglyceride (bearing acetyl, propionyl and butyryl short groups) using the process of this invention. The interesterification reactions of Example 3 are repeated, except that the interesterification mixture contains hydrogenated canola (denoted below as "H-Canola") with triacetin, tripropionin, and tributyrin (in proportions set out below) followed by steam deodorization.

The following M.D.P. and S.F.I. data on the products are obtained:

| H-Canola:Triacetin:Tripropionin:Tributyrin Molar Reactant Ratio | | | |
|---|---|---|---|
| | 1:0.5:1.0:1.0 | 1:0.7:1.4:1.4 | 1:2.4:4.8:4.8 |
| M.D.P., °C. | 35.0 | 31.3 | 26.8 |
| S.F.I. 50° F. | 68.6 | 67.8 | 63.3 |
| 70° F. | 63.2 | 56.5 | 36.1 |
| 80° F. | 42.5 | 29.6 | 1.0 |
| 92° F. | 4.6 | 0.0 | 0.0 |
| 100° F. | 4.6 | 0.0 | 0.0 |

EXAMPLE 5

This example illustrates the diversity of acetoglycerides that can be prepared using the method of this invention.

One product is prepared by randomly interesterifying 4.5 moles triacetin (obtained from Aldrich), 4.5 moles tributyrin (obtained from Schweizerhall), 3.0 moles medium chain triglycerides (Neobee TM M-5, obtained from Stephan, containing about 67.9% $C_8$, 31.1% $C_{10}$, and 0.6% $C_{12}$ fatty acid substituents and used throughout this Example), and 1.0 mole fully hydrogenated soybean oil (obtained from Vandenberg) in the presence of a catalytic amount of sodium methoxide (~0.3%) with vigorous stirring at 100° to 150° C. for 5 to 60 minutes. After cooling the reaction mixture and adding about 5 weight % water, the aqueous phase is removed and the organic phase filtered through bleaching clay. The filtrate is vacuum steam deodorized to yield a fat mixture having a M.D.P. of 17.6° C. and an S.F.C. of 42.8% at 32.0° F., 18.1% at 50° F., 0.3% at 70° F., 0.6% at 80° F., and 0% at 92° F.

Similar results are achieved when 9 moles triacetin and 3 moles medium chain triglycerides are interesterified with 1 mole of the same hydrogenated soybean oil and steam deodorized under the same conditions, yielding a product having a M.D.P. of 22.6° C., and an S.F.C. of 50.5% at 32° F., 30.4% at 50° F., 3.9% at 70° F., 0.2% at 80° F., and 0% at 92° F.

Another product is prepared by interesterifying 1 mole hydrogenated canola (described in Example 1) with 6 moles triacetin and 6 moles medium chain triglycerides (described above) by heating to ~110° C. with agitation in the presence of 0.2 to 0.3% sodium methoxide and steam deodorizing as described in Example 1 to yield a fat product having a M.D.P. of 21° C., and a S.F.I. of 1.5% at 50° F. and 0% at 70° F. and above. Similarly, interesterification of 1 mole hydrogenated canola, 3.48 moles triacetin and 9 moles medium chain triglycerides under the same conditions yields a liquid oil having a M.D.P. of 20.3° C. and no solids at 50° to 100° F.

Yet other products can be made using different reactant ratios in the process of this invention. Interesterification of 1 mole hydrogenated canola, 3.84 moles triacetin, 1.25 moles tripropionin and 0.25 moles medium chain triglycerides followed by steam deodorization yields a product having a M.D.P. of 23.5° C. and an S.F.I. of 60.5% at 50° F., 44.2% at 70° F., 22.5% at 80° F., and 0% at 92° F. Interesterification of 1 mole hydrogenated canola, 0.94 moles triacetin, 3.16 moles tripropionin and 0.33 moles medium chain triglycerides and steam deodorization yields a product having a M.D.P. of 31.5° C. and a S.F.I. of 59.3% at 50° F., 43.0% at 70° F., 25.9% at 80° F., and 0% at 92° F.

Additional desirable mixtures can be achieved by increasing the temperature of the steam deodorization. Random interesterification of 10 moles triacetin and 2.0 moles medium chain triglycerides with 1 mole hydrogenated canola followed by steam deodorization at 260° C. rather than 210° C. for about 2 hours yields a fat mixture having a M.D.P. of 31.8° C.° C. and an S.F.C. of 77.8% at 32° F., 70.8% at 50° F., 45.1% at 70° F., 24.7% at 80° F., 1.1% at 92° F., and 1.8% at 100° F. Likewise, randomly interesterifying 4.5 moles triacetin, 4.5 moles tributyrin and 3.0 moles medium chain triglycerides with 1.0 mole hydrogenated soybean oil followed by steam deodorization at 260° C. for 2 hours yields a mixture having a M.D.P. of 22.2° C., and an S.F.C of 70.5% at 32° F., 52.6% at 50° F., 4.8% at 70° F., 0.2% at 80° F., and 0% at 92° F.

These effects are further illustrated by way of the random interesterification of 6 moles triacetin and 1 mole medium chain triglycerides with 1 mole hydrogenated high erucic rapeseed oil (denoted sample A below), 6 moles triacetin and 2 moles medium chain triglycerides with 1 mole hydrogenated high erucic rapeseed oil (sample B), and 6 moles tributyrin and 2 moles medium chain triglycerides with 1 mole hydrogenated high erucic rapeseed oil (sample C), followed by steam deodorization at 260° C. for 2 hours, yielding mixtures having the following physical properties:

|  | (A) | (B) | (C) |
| --- | --- | --- | --- |
| M.D.P., °C. | 45.1° | 42.1° | 35.1° |
| S.F.C. 32° F. | 88.5% | 82.5% | 74.9% |
| 50° F. | 86.4% | 79.9% | 69.1% |
| 70° F. | 82.1% | 73.1% | 49.5% |
| 80° F. | 77.4% | 64.8% | 31.1% |
| 92° F. | 59.2% | 38.2% | 1.9% |
| 100° F. | 43.2% | 17.6% | 0.1% |
| 104° F. | 28.2% | 4.3% | — |

A variety of triglycerides bearing long chain residues can be used as reactants in the process of this invention. For example, using high erucic rapeseed obtained from CSP, hydrogenated to an IV$\leq$3 (hereafter denoted H-HEAR), in the interesterification reaction, followed by steam deodorization at 210° C. as described above yields acetoglycerides exhibiting the following properties:

| H-Canola:H-HEAR:Triacetin:Tripropionin Reactant Molar Ratio | | | | | |
| --- | --- | --- | --- | --- | --- |
|  | 0.9:0.1: 11:1 (D) | 0.9: 0.1:5:3 (E) | 0.9:0.1:6:6 (F) | 0.9:0.1:1:11 (G) | 0.9:0.1:3:9 (H) |
| M.D.P., °C. | 35.4° | 33.0° | 30.4° | 31.0° | 30.8° |
| S.F.I. 50° F. | 70.2 | 68.7 | 58.9 | 64.6 | 60.5 |
| 70° F. | 68.4 | 64.1 | 46.9 | 53.1 | 47.3 |
| 80° F. | 63.8 | 52.3 | 28.4 | 26.2 | 23.4 |
| 92° F. | 33.1 | 7.2 | 0.3 | 0 | 0 |
| 100° F. | 0.2 | 0 | 0.2 | 0 | 0 |

Substituting medium chain triglycerides for the tripropionin in the interesterification mixture results in the following triglyceride mixtures:

| H-Canola:H-HEAR:Triacetin:MCT Reactant Molar Ratio | | | |
| --- | --- | --- | --- |
|  | 0.9:0.1:5.7:0.3 (I) | 0.9:0.1:8.6:3.4 (J) | 0.9:0.1:5.7:6.3 (K) |
| M.D.P., °C. | 34.3° | 24.5° | 11.1° |
| S.F.I. 50° F. | 63.5 | 30.9 | 1.3 |
| 70° F. | 56.3 | 6.5 | 0 |
| 80° F. | 46.3 | 0 | 0 |
| 92° F. | 16.2 | 0 | 0 |
| 100° F. | 0.4 | 0 | 0 |

Again, varying the processing conditions varies the product. Steam deodorizing sample K at 260° C. rather than 210° C. yields a product that had an M.D.P. of 19.6° C. and 19.8% solids at 50° F., with no solids at 70° to 100° F.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are meant to cover the claimed components and steps in any sequence which is effective to meet the objectives there intended, unless the context specifically indicates the contrary.

We claim:

1. A solventless process for synthesizing triglycerides bearing acetyl and long $C_{16}$ to $C_{22}$ fatty acid residues which comprises interesterifying triglycerides bearing long $C_{16}$ to $C_{22}$ fatty acid residues, at least 70% of which are stearic acid residues, with triacetin and triglycerides bearing saturated $C_3$ to $C_{10}$ acid residues in a single phase in the presence of a catalyst at a temperature varying between 100° C. and 150° C.

2. A process according to claim 1 wherein the interesterification is carried out at a temperature varying between about 120° and 135° C.

3. A process according to claim 1 wherein the triglycerides bearing saturated $C_3$ to $C_{10}$ acid residues are selected from the group consisting of tripropionin, tributyrin and a mixture of tripropionin and tributyrin.

4. A process according to claim 1 wherein the triglycerides bearing saturated $C_3$ to $C_{10}$ acid residues consist essentially of triglycerides bearing $C_8$ to $C_{10}$ acid residues.

5. A process according to claim 1 wherein the triglycerides bearing saturated $C_3$ to $C_{10}$ acid residues are a mixture of triglycerides bearing saturated $C_8$ to $C_{10}$ acid residues and triglycerides selected from the group consisting of tripropionin, tributyrin, and a mixture of tripropionin and tributyrin.

6. A process according to claim 1 wherein the long acid residues are saturated.

7. A process according to claim 6 wherein at least about 85% of the long acid residues are stearic acid residues.

8. A process according to claim 1 wherein the reactant molar ratio of triglycerides bearing long $C_{16}$ to $C_{22}$ fatty acid residues to triacetin and triglycerides bearing $C_3$ to $C_{10}$ acid residues varies between 1:1 and 1:15.

9. A process according to claim 8 wherein the ratio varies between 1:3 and 1:12.

10. A process according to claim 1 wherein the catalyst is selected from the group consisting of an alkali metal alkoxide, sodium, potassium, and a sodium/potassium alloy.

11. A process according to claim 10 wherein the catalyst is selected from the group consisting of sodium methoxide, potassium methoxide, lithium methoxide, sodium ethoxide, potassium ethoxide, lithium ethoxide, sodium propoxide, potassium propoxide, lithium propoxide, sodium butoxide, potassium butoxide, and lithium butoxide.

12. A process according to claim 11 wherein the catalyst is sodium methoxide.

13. In a process for interesterifying a fully hydrogenated oil with triacetin in the presence of a catalyst an improvement wherein triglycerides bearing $C_3$ to $C_{10}$ acid residues are added to the reaction mixture to form a single phase, and the reaction is conducted in the absence of solvent at a temperature varying between 100° and 150° C.

14. An improvement according to claim 13 wherein the reaction is conducted at a temperature varying between about 120° and 135° C.

15. An improvement according to claim 13 wherein triglycerides bearing $C_3$ to $C_{10}$ acid residues are selected from the group consisting of tripropionin, tributyrin, $C_8$ to $C_{10}$ triglycerides and mixtures of these.

16. An improvement according to claim 15 wherein the triglycerides bearing $C_3$ to $C_{10}$ acid residues consists essentially of tripropionin.

17. An improvement according to claim 16 wherein the molar ratio of fully hydrogenated oil to triacetin and tripropionin varies between 1:3 and 1:12.

18. An improvement according to claim 17 wherein the molar ratio of fully hydrogenated oil to triacetin to tripropionin is 1:11:1.

19. In a process for reacting a fully hydrogenated oil with triacetin in the presence of an alkali metal alkoxide catalyst by agitating and heating the reaction mixture to a temperature of less than 120° C., an improvement wherein tripropionin is added to the reaction mixture and the reaction is conducted in a single phase in the absence of solvent.

20. An improvement according to claim 19 wherein the temperature varies from 120° C. to 150° C.

21. An improvement according to claim 18 wherein the temperature varies from about 120° and 135° C.

22. An improvement according to claim 19 wherein the molar ratio of fully hydrogenated oil to triacetin and tripropionin varies between 1:1 and 1:15.

23. An improvement according to claim 22 wherein the alkali metal alkoxide catalyst is sodium methoxide and the fully hydrogenated oil is selected from the group consisting of hydrogenated canola, hydrogenated soybean oil, hydrogenated high erucic rapeseed oil, and mixtures thereof.

24. A solventless process for synthesizing triglycerides bearing acetyl and saturated $C_{16}$ to $C_{22}$ fatty acid residues which comprises interesterifying triglycerides bearing saturated $C_{16}$ to $C_{22}$ fatty acid residues with tracetin in the presence of triglycerides bearing saturated $C_3$ to $C_{10}$ acid residues and a catalyst in a single phase at a temperature varying between about 100° and about 150° C., wherein the reactant molar ratio of triglycerides bearing saturated fatty acid residues to triacetin and triglycerides bearing $C_3$ to $C_{10}$ acid residues varies between 1:3 and 1:12.

25. A process according to claim 24 wherein the triglycerides bearing saturated $C_{16}$ to $C_{22}$ fatty acid residues is a fully hydrogenated vegetable oil.

26. A process according to claim 25 wherein the fully hydrogenated vegetable oil is selected from the group consisting of hydrogenated soybean oil, safflower oil, sunflower oil, sesame oil, peanut oil, corn oil, olive oil, rice bran oil, mustard seed oil, cottonseed oil, poppyseed oil, rapeseed oil, marine oil, and meadowfoam oil, and mixtures thereof.

27. A process according to claim 24 wherein the triglycerides bearing saturated $C_3$ to $C_{10}$ acid residues are selected from the group consisting of tripropionin, tributyrin, and a mixture of tributyrin and tripropionin.

28. A process according to claim 27 wherein the triglycerides bearing saturated $C_{16}$ to $C_{22}$ fatty acid residues is a fully hydrogenated vegetable oil.

* * * * *